United States Patent [19]
Anderson

[11] 4,177,770
[45] Dec. 11, 1979

[54] COMPENSATION OF SENSOR VOLTAGE FOR REFERENCE POTENTIAL VARIATION

[75] Inventor: Robert L. Anderson, Saline, Mich.

[73] Assignee: Ford Motor Company, Dearborn, Mich.

[21] Appl. No.: 940,421

[22] Filed: Sep. 7, 1978

[51] Int. Cl.² ............................ F02B 3/08; F01N 3/08
[52] U.S. Cl. .......................... 123/32 EE; 123/119 EC; 60/276; 60/285
[58] Field of Search ........ 123/32 EE, 32 EA, 32 EF, 123/119 EC; 60/276, 285

[56] References Cited

U.S. PATENT DOCUMENTS

| | | | |
|---|---|---|---|
| 3,948,081 | 4/1976 | Wessel et al. | 60/276 |
| 4,019,474 | 4/1977 | Nishimiya et al. | 123/32 EE |
| 4,117,815 | 10/1978 | Ikeura | 60/276 |
| 4,120,269 | 10/1978 | Fujishiro | 123/32 EE |
| 4,140,085 | 2/1979 | Rabus et al. | 123/32 EE |

Primary Examiner—Charles J. Myhre
Assistant Examiner—P. S. Lall
Attorney, Agent, or Firm—Robert W. Brown; Clifford L. Sadler

[57] ABSTRACT

An improved electrical system particularly suitable for use in a motor vehicle. The improvement provides compensation of a signal used in association with an electronic circuit. Such compensation is made necessary because of variation in the potential that occurs at a source of electrical energy in the system relative to the sensor reference potential. The variation in potential results from currents flowing through a conductor interconnecting the sensor and the energy source, which current many be of varying character due to the operation of other devices associated with the system. Compensation is achieved with a differential amplifier coupled both to the energy source and to the sensor.

10 Claims, 2 Drawing Figures

COMPENSATION OF SENSOR VOLTAGE FOR REFERENCE POTENTIAL VARIATION

BACKGROUND OF THE INVENTION

This invention relates to an improved electrical system wherein compensation is provided for a sensor signal to which an electronic circuit responds so that variations in current within the system do not effect the response of the electronic circuit to the sensor signal. The invention is particularly suitable for use in conjunction with a motor vehicle electrical system.

It has become general practice in the design of motor vehicles to provide storage batteries as a source of DC electrical energy, starter motors supplied with energy from the DC source, and alternator systems for charging the DC source during normal operation of the engine. Typical reference potential or grounding practice provides a conductive strap that interconnects the negative terminal of the battery with the vehicle's engine block, thereby, providing a "common" or "ground" reference potential throughout the motor vehicle.

In recent times, the application of electronic devices to motor vehicles has increased. Electronic control units associated with engine or other vehicle systems are supplied with sensor signal voltages representing parameters of engine or vehicle operation. Some of these sensors provide very low voltage signals that are used by digital electronic circuits which achieve some desired control function.

One such sensor is an exhaust-gas-oxygen (EGO) sensor that is mounted in the exhaust conduit from the engine and that provides a signal in the millivoltage range representative of the partial pressure of oxygen in the exhaust stream emanating from the engine. When the mixture of air and fuel supplied to the engine is rich, the EGO sensor provides a voltage in the range from about 800 to 900 millivolts, and when the mixture supplied to the engine is lean, the sensor output voltage is in the zero to 100 millivolt range. A rapid transition between the two voltage levels occurs when the mixture supplied to the engine changes from rich to lean and vice versa.

The EGO sensor typically is of the zirconia type commercially available and is threadedly connected to the exhaust conduit from the engine, which exhaust conduit is made from a conductive material, and the sensor has a single lead wire from it connected to an electronic unit controlling the air-fuel ratio supplied to the engine. The reference potential for the sensor is a terminal attached electrically to the exhaust conduit at a location near the EGO sensor. This connection is coupled to the electronic circuit associated with the sensor.

Unfortunately, during cranking of the engine and during engine operation, the current flowing between the engine block and the negative or source reference terminal of the DC source of electrical energy, the battery, is substantial. For example, during engine cranking, this current may be 40 amperes or more and a small resistance between the engine block and the negative terminal of the battery of, for example, 0.20 ohms is sufficient to produce an 800 millivolt voltage drop across the ground strap or cable interconnecting the negative terminal of the battery and the engine block. Since the negative terminal of the battery typically is directly coupled to the electronic control unit associated with the EGO sensor and since there is a variable voltage drop in the ground strap interconnecting the engine block and the negative terminal of the battery, the sensor voltage signal may be completely lost, may be ignored by the electronic circuitry associated with the sensor, or may be of a level such that the electronic circuit cannot detect voltage levels or transitions between voltage levels.

SUMMARY OF THE INVENTION

An improved electrical system according to the invention comprises a source of electrical energy having a source reference terminal and another terminal across which is developed a potential difference usable as a supply voltage for the electrical system. Means are provided for generating a sensor signal voltage between first and second terminals, and an electronic circuit is provided and adapted to respond to the signal voltage. The electronic circuit uses the potential at the source reference terminal as its reference potential. Conductive means electrically couple the first terminal of the sensor signal generating means to the source reference terminal. Also, the electrical system includes means for causing currents of varying character to flow through the conductive means.

Within the above environment, the improvement of the invention comprises means for generating a compensated signal voltage. The compensated signal voltage is equal or proportional to the sensor signal voltage as it appears across the first and second terminals mentioned above. The compensated signal voltage is referenced to the potential of the source reference terminal and is compensated, as compared to the voltage between the second terminal of the sensor signal generating means and the source reference terminal, for varying potential differences appearing across the conductive means as a result of the currents of varying character flowing through such conductive means.

The invention is particularly useful in a motor vehicle electrical system having an EGO sensor. The electronic circuit associated with the EGO sensor may be of a digital or microprocessor type and, therefore, may use the negative terminal of the DC source of electrical energy, or battery in the motor vehicle as its reference, rather than employing the engine block or vehicle body as a potential reference, because electrical noise difficulties are avoided thereby. Of course, the negative terminal of the battery and the engine block would be electrically interconnected with a ground strap and for most other purposes may be regarded as electrically equipotential locations.

The invention may better be understood by reference to the detailed description that follows and to the drawings.

DETAILED DESCRIPTION OF THE INVENTION

Figure 1:
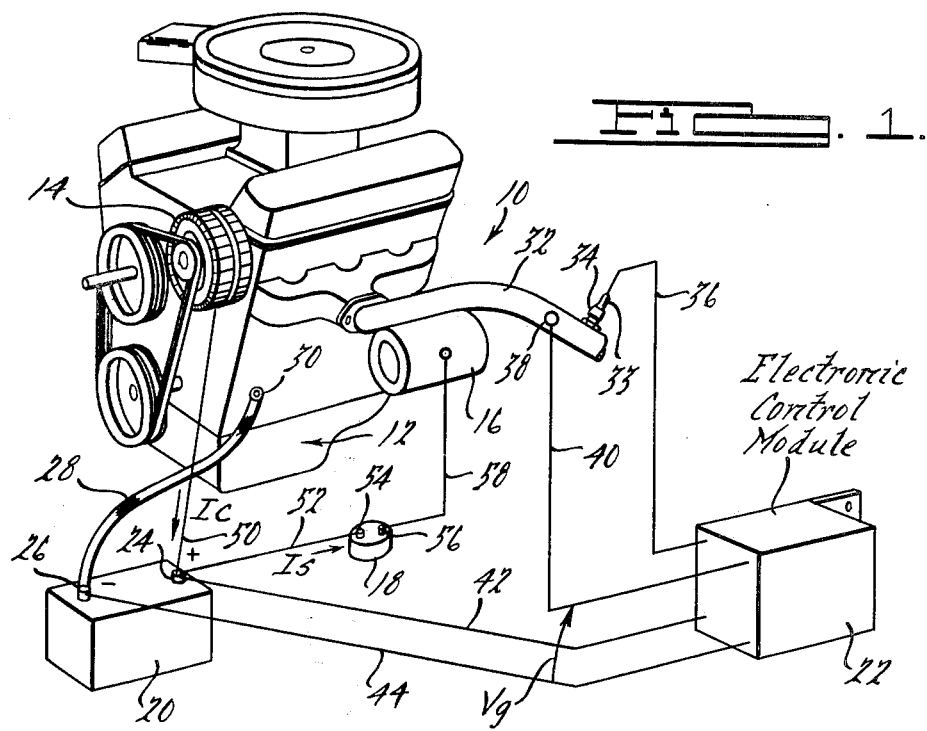
FIG. 1 is a schematic electrical diagram of an improved electrical system in accordance with the invention.

With reference now to the drawings, wherein like numerals refer to like parts in the views, there is shown an electrical system 10 for a motor vehicle. The motor vehicle (not shown) includes an engine 12 the main components of which are made from conductive materials, such as is the engine block. The engine 12 includes an alternator 14 used for charging the vehicle's source of electrical energy 20, a DC storage battery, and also used for supplying electrical energy to various devices during normal engine operation.

The electrical system 10 includes a starter motor 16 connected by a solenoid switching device 18 to the positive terminal 24 of the battery 20. The negative terminal 26 of the battery is connected by a conductive ground strap 28 to the engine block 30. The electrical system 10 also includes an electronic control module 22 that is associated with an exhaust gas oxygen sensor 34 having a lead 36 supplying the sensor signal potential appearing on sensor terminal 33 to the electronic control module.

The EGO sensor 34 may be of the solid electrolyte (e.g., zirconia) or variably resistive (e.g., titania) types. Here, the EGO sensor is assumed to be of the zirconia type commercially available and this EGO sensor produces an electromotive force (EMF) that is proportional to the ratio of the logarithm of the atmospheric oxygen pressure and the oxygen pressure in the exhaust stream emanating from the engine. The EFM is the voltage existing between leads 36 and 40, the latter lead being the sensor reference lead conductively connected at terminal 38 to the exhaust conduit 32 leading from the engine 12. Thus, EGO sensor terminal 33 and terminal 38 together constitute first and second terminals, respectively, across which the sensor signal voltage appears and this signal is supplied via leads 36 and 40 to the electronic control module 22.

The electronic control module 22 receives its supply voltage input via leads 42 and 44, lead 44 being connected to the source reference 26 of the battery 20. This source reference connection to the module 22 is particularly desirable where digital electronic systems are employed because thereby engine electrical noise effects on the electronic system are less pronounced than might otherwise be the case.

In the absence of current flow through the ground strap 28, it is clear that terminals 26 and 30 are at the same electrical potential. Moreover, because of the very large mass of conductive material between terminal 38 and terminal 30, there is no voltage drop of significance between these terminals even when there is current flow through the engine block.

Now if it is assumed that the engine is being cranked to cause it to start, the solenoid 18 will be energized by an ignition switch, not shown, in the motor vehicle to provide connection between its terminals 54 and 56. This permits current Is to flow from the battery positive terminal 24 and through lead 52, the solenoid 18, and lead 58 to the starter motor 16. The starter motor thereby is energized and causes the engine to be cranked. Under this circumstance, the return current to the negative terminal 26 of the battery is through the ground strap 28 and in the direction from its terminal 30 to the battery terminal 26. During this cranking mode of operation, the current flowing through the ground strap 28 may be 40 amperes or more and a significant voltage drop may occur between terminals 30 and 26. Since terminal 30 and terminal 38 still are at substantially the same potential despite this large current because of the large mass of conductive material in the engine and manifold, the voltage drop across the ground strap 28 is very nearly equal to the voltage Vg appearing across leads 40 and 44 as shown. The voltage Vg under this circumstance is positive with respect to the negative terminal 26 of the battery 20.

After the vehicle's engine has started, the solenoid 18 is de-energized and the path between its terminals 54 and 56 is open. The revolving crankshaft of the engine drives the alternator 14 causing it to produce a rectified output voltage that provides DC charging current Ic flowing through lead 50 to the positive terminal of the battery. The alternator 14 is connected to the engine block electrically and the return path, to the alternator, for the battery charging current is through the ground strap 28, but the direction of flow is from the negative terminal 26 of the battery 20 to the terminal 30 on the engine block. As a result, the voltage Vg under such circumstance is negative relative to the potential of the source reference terminal 26. The voltage drop across the ground strap 28 again may be quite significant with respect to the sensor signal voltage output appearing between terminals 33 and 38, the aforementioned first and second terminals of the sensor 34. If the electronic control module 22 is to be responsive to the sensor signal voltage, it is desirable that compensation be made for the variation in potential caused by the currents of varying character that flow through the ground strap 28.

The improvement of the present invention provides means for generating a compensated sensor signal voltage. The compensated signal voltage is equal or proportional to the sensor signal voltage appearing between terminals 33 and 38, but is referenced to the potential of the source reference terminal 26, which also is the source reference terminal for the circuitry of the electronic control module 22. The compensated signal is thereby compensated for varying potential differences that appear across the ground strap 28 as a result of currents of varying amplitude and direction that flow therethrough.

Figure 2:
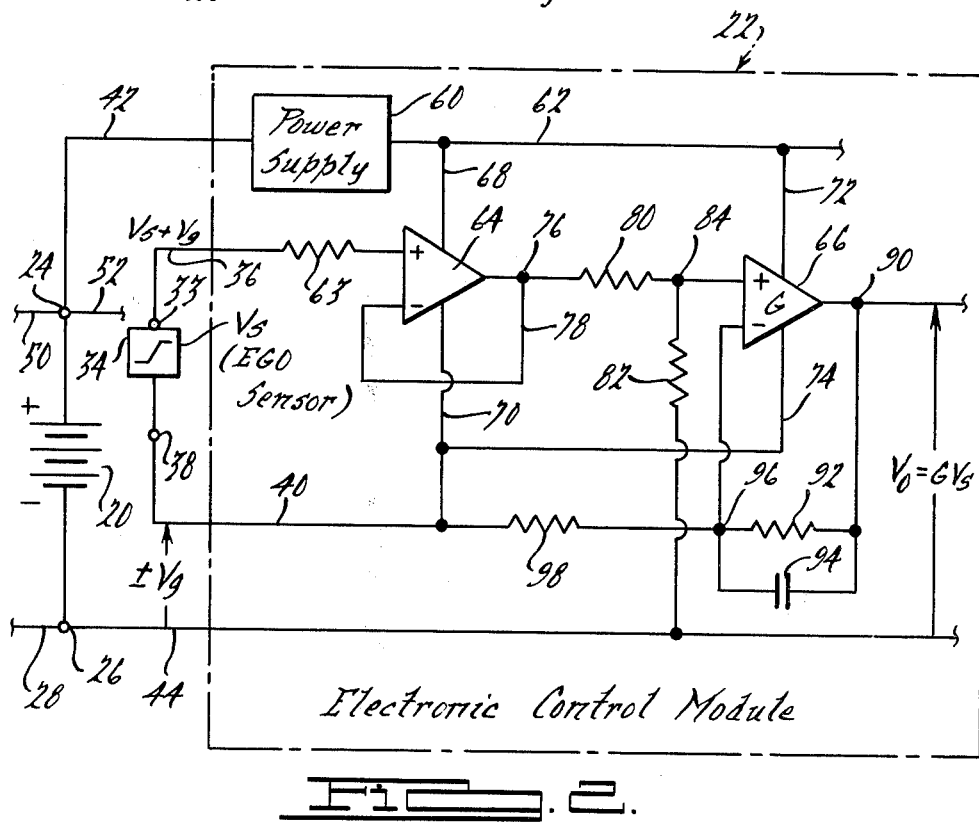
FIG. 2 is a schematic electrical diagram of the electrical system of FIG. 1 and includes a detailed schematic circuit preferably included in an electronic control module illustrated in block form in FIG. 1.

In FIG. 2 there is shown in more schematic detail the electronic control module 22 and, in particular, a portion of the circuitry therein suitable for use in generating the aforementioned compensated sensor signal voltage.

The circuitry in the control module 22 is supplied with electrical energy from the terminals 24 and 26, the latter being the source reference terminal. The electronic control module 22 may include an internal power supply 60 which typically would be used to provide a regulated DC supply volage, referenced to the potential on source reference lead 44, for the various electronic circuits therein. The regulated supply voltage appears between leads 62 and 44. Leads 68 and 72 couple the regulated voltage on lead 62 to the differential amplifiers 64 and 66, respectively. However, the negative supply leads for these amplifiers are coupled by leads 70 and 74 to the lead 40 which is connected to terminal 38 on the exhaust manifold of the engine. The connection of amplifier supply leads 70 and 74 to lead 40 and terminal 38, rather than to the source reference potential lead 44, permits the compensation circuitry of the invention to respond to voltages Vg which are both positive and negative.

The voltage produced by the EGO sensor is designated Vs and is the potential difference between its first and second terminals 33 and 38. This voltage plus the voltage Vg is the total voltage, relative to the source reference 44, that is supplied through an input resistor 63 to the positive input terminal of the amplifier 64, which is connected as a voltage follower. The output terminal 76 of the amplifier 64 is connected by lead 78 to its negative input terminal to produce the voltage-follower characteristic. The voltage-follower acts as a high-input impedance for the circuitry in the electronic control module to minimize loading effects on the EGO sensor 34.

The voltage Vs plus Vg appearing at terminal 76 is applied to a voltage divider connected between this terminal and the source reference lead 44. The voltage divider includes resistors 80 and 82. The junction 84 between the resistors is connected to the positive terminal of the differential amplifier 66. The voltage Vg appearing on lead 40 is supplied through input resistor 98 to the terminal 96 connected to the negative input of the differential amplifier 66. The output terminal 90 of differential amplifier 66 is coupled to the negative input thereof by negative feedback components including resistor 92 connected in parallel with filter capacitor or high-frequency roll-off capacitor 94. Resistors 92 and 98 determine the gain of the differential amplifier 66 so that the output voltage Vo appearing at terminal 90 is equal to the gain G of the differential amplifier 66 times the sensor voltage signal Vs. The output voltage Vo is used by circuitry, not specifically shown, in the electronic control module 22.

The ratio of the value of the resistor 92 to that of the resistor 98 establishes the overall circuit gain G. The voltage divider comprising resistors 80 and 82 is required to compensate for the higher gain of the differential amplifier 66 with positive input than with a negative input. Design of the compensation circuitry, in order eliminate any contribution due to Vg in the output signal and make Vo strictly a function of Vs (Vo=GVs), requires that resistors 80 and 82 have values $R_{80}$ and $R_{82}$ such that:

$$\frac{R_{82}}{R_{80} + R_{82}} = \frac{G}{G + 1}$$

From the above it is seen that the electrical system of the invention is improved in that it provides a compensated sensor signal voltage Vo that is equal or proportional to the voltage Vs produced by a sensor in the electrical system and that the signal VO proportional to Vs is referenced to the potential of a source reference terminal 26 rather than to the potential of the terminal 38 against which the sensor voltage Vs is referenced. Thus, the improvement of the invention permits an electronic circuit in the module 22 to respond to the signal produced by a sensor in an electrical system while at the same time compensating in the system for the potential variations produced at the sensor due to currents of varying character flowing through conductive means interconnecting a source of electrical energy of the electrical system with the sensor location.

Based upon the foregoing description of the invention, what is claimed is:

1. An improved electrical system of the type which comprises:
   (a) a source of electrical energy having a source reference terminal and an other terminal across which terminals is developed a potential difference or EMF usable as a supply voltage for said electrical system;
   (b) means for generating a sensor signal voltage, said means having first and second terminals across which said sensor voltage is generated;
   (c) an electronic circuit adapted to respond to said sensor signal voltage, said electronic circuit using the potential at said source reference terminal as the reference potential for said electronic circuit;
   (d) conductive means for coupling said second terminal of said signal generating means to said source reference terminal; and
   (e) means for causing currents of varying character to flow through said conductive means;
   wherein the improvement comprises:
   (f) means for generating a compensated sensor signal voltage, said compensated sensor signal voltage being equal or proportional to said sensor signal voltage as it appears across said first and second terminals, said compensated sensor signal voltage being referenced to the potential of said source reference terminal and being compensated, as compared to the voltage between said first terminal of said signal generating means and said source reference terminal, for varying potential differences appearing across said conductive means as a result of said currents of varying character flowing therethrough.

2. An improved electrical system according to claim 1, wherein said means for generating said compensated sensor signal voltage comprises a differential amplifier having first and second inputs and an output at which said compensated signal voltage appears, means for supplying said first input of said differential amplifier with a voltage proportional to the potential difference between said first terminal of said means for generating said sensor signal voltage and said source reference terminal of said source of electrical energy, and means for supplying to said second input of said differential amplifier a voltage proportional to the potential difference between said second terminal of said means for generating a sensor signal voltage and said source reference terminal of said source of electrical energy.

3. An improved electrical system according to claim 2, wherein said means for supplying said voltage to said first input of said differential amplifier comprises a voltage divider coupled between said first terminal of said means for generating said sensor signal voltage and said source reference terminal of said source of electrical energy.

4. An improved electrical system according to claim 3, wherein said means for supplying said voltage to said differential amplifier further comprises a voltage follower for providing high-input-impedance coupling of said first terminal of said means for generating said sensor signal voltage to said voltage divider.

5. An improved electrical system according to claim 3, wherein said differential amplifier has a supply voltage input connected to said second terminal of said means for generating said sensor signal voltage.

6. An improved electrical system according to claim 4, wherein said differential amplifier and said voltage follower have common supply voltage inputs, one of said supply voltage inputs being connected to said second terminal of said means for generating said sensor signal voltage.

7. An improved electrical system according to claim 6, wherein said electrical system further includes means for causing bidirectional currents to flow in said conductive means for coupling said second terminal of said means for generating said sensor signal voltage to said source reference terminal.

8. An improved electrical system according to claim 7, wherein said electrical system is an electrical system for a motor vehicle having an engine, wherein said source of electrical energy is a storage battery, having positive and negative terminals, one of said terminals being said source reference terminal, and wherein said conductive means comprises a ground strap interconnecting said source reference terminal of said storage battery with said engine.

9. An electrical system according to claim 8, wherein said means for generating said sensor signal voltage is an exhaust gas sensor generating an electromotive force or voltage proportional to the amount of oxygen in the exhaust stream emanating from said engine during its operation.

10. An improved electrical system according to claim 9, wherein said electronic circuit includes a digital electronic microprocessor.

* * * * *